(12) United States Patent
Stagg

(10) Patent No.: US 7,167,240 B2
(45) Date of Patent: Jan. 23, 2007

(54) CARBON BLACK SAMPLING FOR PARTICLE SURFACE AREA MEASUREMENT USING LASER-INDUCED INCANDESCENCE AND REACTOR PROCESS CONTROL BASED THEREON

(75) Inventor: Barry James Stagg, Acworth, GA (US)

(73) Assignee: Columbian Chemicals Company, Marietta, GA (US)

( * ) Notice: Subject to any disclaimer, the term of this patent is extended or adjusted under 35 U.S.C. 154(b) by 547 days.

(21) Appl. No.: 10/622,318

(22) Filed: Jul. 18, 2003

(65) Prior Publication Data

US 2004/0046957 A1    Mar. 11, 2004

Related U.S. Application Data

(60) Provisional application No. 60/397,428, filed on Jul. 19, 2002.

(51) Int. Cl.
*G01N 21/00* (2006.01)
(52) U.S. Cl. ..................................... 356/337
(58) Field of Classification Search ..................... None
See application file for complete search history.

(56) References Cited

U.S. PATENT DOCUMENTS

| | | | |
|---|---|---|---|
| 4,355,016 A | 10/1982 | Stacy et al. | |
| 4,436,698 A | 3/1984 | Stacy et al. | |
| 4,605,535 A | 8/1986 | Dimpfl | 422/95 |
| 5,049,369 A | 9/1991 | Howell | |
| 5,109,708 A | 5/1992 | Lawless | 73/863.11 |
| 5,211,932 A | 5/1993 | Blaylock et al. | 423/450 |
| 5,423,228 A | 6/1995 | Budd et al. | 73/863.21 |
| 5,920,388 A * | 7/1999 | Sandberg et al. | 356/315 |
| 6,154,277 A | 11/2000 | Snelling et al. | |

(Continued)

FOREIGN PATENT DOCUMENTS

DE    24 27 908 A1    1/1976

(Continued)

OTHER PUBLICATIONS

Dec, J.E., Zur Loye, A.O., and Siebers, D.L., "Soot distribution in a D.I. Diesel Engine Using 2-D Laser Induced Incandescence Imaging," *SAE Transactions*, 100, pp. 277-288 (1991).

(Continued)

*Primary Examiner*—Tu T. Nguyen
(74) *Attorney, Agent, or Firm*—Needle & Rosenberg, P.C.

(57) ABSTRACT

Disclosed is a method for in-situ sampling and measuring particulate fineness in a process stream, comprising (a) sampling particles in-situ from a process stream, (b) adjusting the sample to conditions suitable for LII, (c) measuring the fineness using LII, and (d) correlating the LII fineness measurement with actual particle fineness. Also disclosed is a method for sampling and controlling a process based on the real-time, on-line, in-situ methods for sampling and measuring particles. Sampling can comprise drawing a sidestream from a source of the particles. Adjusting the sample to conditions suitable for LII can comprise diluting the sample or bringing the temperature of the sample to ambient conditions. Correlating may comprise using a correlation function determined by comparing LII measurements and laboratory fineness measurements for particle samples drawn at the same time.

27 Claims, 8 Drawing Sheets

U.S. PATENT DOCUMENTS 6,181,419 B1    1/2001   Snelling et al.

FOREIGN PATENT DOCUMENTS

EP    0 638 796 A1    2/1995
WO    WO 97/30335    8/1997

OTHER PUBLICATIONS

Snelling, D.R., Smallwood, G.J., Gülder, Ö.L., Liu, F., and Bachalo, W.D., "A Calibration-Independent Technique of Measuring Soot by Laser-Induced Incandescence Using Absolute Light Intensity," The Second Joint Meeting of the U.S. Sections of the Combustion Institute, Oakland, California, Mar. 25-28 (2001).

Starke, R. and Roth, P., "Soot Particle Sizing by LII During Shock Tube Pyrolysis of $C_6H_6$," *Combustion and Flame*, 127(4):2278-2285 (2002).

* cited by examiner

CARBON BLACK SAMPLING FOR PARTICLE SURFACE AREA MEASUREMENT USING LASER-INDUCED INCANDESCENCE AND REACTOR PROCESS CONTROL BASED THEREON

CROSS REFERENCE TO RELATED APPLICATIONS

This application claims priority to U.S. Provisional Application No. 60/397,428 filed Jul. 19, 2002, hereby incorporated by reference in its entirety.

BACKGROUND OF THE INVENTION

1. Field of the Invention

This invention relates generally to methods of sampling particles, especially carbon black, for measuring fineness, or particle surface area, and methods of controlling carbon black reactors.

2. Background

The current method of determining carbon black fineness (surface area) during the manufacturing process is to collect a sample, take it to the lab, and then determine the fineness via $I_2$ or $N_2$ absorption methods. This gives a delay time of at least about an hour. Therefore, several hours of "off-spec" carbon black could be produced while "lining out" the reactor conditions (adjusting reactor conditions in response to the fineness measurements which come from the lab to bring the carbon black into specification), since several iterations are usually required to achieve the product specification targets.

There has, therefore, been a long felt need in the carbon black industry for in-situ sampling and measurement of carbon black fineness during the manufacturing process so that adjustments can be made to the process more quickly. It is desired to provide real-time, on-line sampling and fineness (particle surface area) measurements of carbon black while the carbon black is being manufactured.

Laser-induced incandescence (LII) has been used as a soot diagnostic technique since about the 1980s. The basic principle of LII is to rapidly heat up particles with ultra-short laser pulses (laser pulse is typically <20 ns duration) of high energy. Particle temperature is increased to a point to produce significant incandescence of the particle, or even up to vaporization temperature (for carbon blacks, about 4000 K). Particles lose this added energy via 3 paths: vaporization, heat conduction to the surrounding medium, and thermal radiation. The enhanced thermal radiation is then detected (emission signal). The incandescence from the particles is measured using collection optics and photo detectors. Using appropriate calibration and analysis of the incandescence signal, information such as the soot volume fraction (svf) or the primary soot particle size may be obtained. The method is essentially non-intrusive and is capable of making in-situ measurements.

LII measurement is an emerging technology that has promise to be a reliable means for spatially and temporally measuring the concentration of carbonaceous particles and their spherule size. LII has been developed primarily for monitoring particulate emissions produced by combustion of hydrocarbon fuels. In the past 10 years or so, academic researchers have utilized LII to resolve spatial concentrations of soot in laboratory flames and diesel engines (See, e.g., Dec, J. E., zur Loye, A. O., and Siebers, D. L., "Soot distribution in a D.I. Diesel Engine Using 2-D Laser Induced Incandescence Imaging," SAE Transactions, 100, pp. 277–288, 1991).

LII is suitable for soot particulate measurements since the LII signal is proportional to particulate volume faction over a wide dynamic range. LII provides a relative measure of soot concentrations and requires a calibration for quantification of soot particulate concentrations. LII has been used to measure soot particle volume fraction in steady-state and time-varying diffusion flames, premixed flames within engines and in diesel engine exhaust streams, and gas turbine exhausts. These LII applications are with relatively dilute (low concentration) streams of soot.

Recently, a technique for performing absolute light intensity measurement in LII has been presented, thus avoiding the need for a calibration in a source of soot particulates with a known concentration (U.S. Pat. No. 6,154,277), and, thus, extending the capabilities of LII for making practical quantitative measurements of soot. Using this in-situ absolute intensity self-calibration technique, LII has been applied to measure soot particle volume fraction in laminar diffusion flames, carbon black, and in diesel engine exhaust streams. See, e.g., Snelling, D. R., Smallwood, G. J., Gülder, Ö. L., Liu, F., and Bachalo, W. D., "A Calibration-Independent Technique of Measuring Soot by Laser-Induced Incandescence Using Absolute Light Intensity," The Second Joint Meeting of the U.S. Sections of the Combustion Institute, Oakland, Calif., Mar. 25–28, 2001.

It has also been theorized that LII could be used to measure primary particle size. Some work toward using LII for size (sample particle diameter) measurements of soot and carbon black were published by various academic groups. See, e.g., U.S. Pat. No. 6,181,419; WO 97/30335; and Starke, R. and Roth, P., "Soot Particle Sizing by LII During Shock Tube Pyrolysis of $C_6H_6$," Combustion and Flame, 127:2278–2285 (2002) (the disclosures of which are hereby incorporated by reference for their general teaching on LII methods for determining particle size and LII apparatus/instrumentation used in determining particle size).

For determination of soot concentration, the analysis of the incandescence signal at one point in time (just after the laser pulse) is usually sufficient. However, since heat conduction is mainly governed by particles' specific surface areas, the cooling rate is a characteristic measure for primary particle size, since larger particles will cool more slowly than smaller particles (note: cooling rate time constants are on the order of 1000 ns). The determination of particle fineness requires that the incandescence signal be measured as a function of time while the particles cool. Basically, the dependence between signal decay time and primary particle size is proportional, i.e., smaller particles show lower decay times, but it is generally not linear. Time-resolved LII (TIRE-LII) yields primary particle size by comparing measured temporal signal decay to calculated decays. In order to increase the precision of the technique, since a single data point is collected very quickly, it is common to average the incandescence data from many laser pulses. A typical set up may use a laser with a 20 Hz repetition rate and average the data from 40 pulses, giving a single data point every 2 seconds.

A photomultiplier can be used to measure the temporal signal behavior. The signal is recorded with a fast oscilloscope connected to a computer. Data is read out and a fit provides the characteristic signal decay time. This time is unambiguously connected with primary particle size under certain environmental conditions. If capturing the exact value of primary particle size is desired, known ambient conditions, particularly temperature, are required. The detection of change requires fairly constant conditions or accordingly, information about the temperature change.

Aside from any difficulties in choosing a method that provides real-time on-line measurements, many problems are present in providing particle samples to a chosen method. In using the LII technique for in-situ measurement, appropriate in-situ techniques for pulling and preparing the sample of carbon black must be provided in order to accurately and consistently perform the in-situ measurements.

Problems with sampling, adjusting samples, and measuring samples include plugging of lines used to sample, consistent sample dilution, moisture condensation in sampling lines, and fouling of optical windows.

Once in-situ, real-time sampling and measurement of carbon black can be performed, the tools for real-time process control of carbon black processes are available. By solving the problems of the prior art, the present invention is able to more quickly and reliably control carbon black production processes.

SUMMARY OF THE INVENTION

In accordance with the purpose(s) of this invention, as embodied and broadly described herein, this invention discloses various methods.

The invention includes an in-situ method for sampling a particle-containing stream and measuring particle fineness using laser-induced incandescence (LII) comprising
 a) sampling particles in-situ,
 b) adjusting the sample to conditions suitable for LII,
 c) measuring the adjusted sample using LII, and
 d) correlating the LII measurements with actual particle fineness.

The method can further comprise determining a correlation function by comparing LII measurements and laboratory fineness measurements for particle samples drawn at the same time.

The method can perform the sampling and measurement of particle fineness in real-time and online.

The particles can be carbon black and the particle-containing stream can be in a carbon black reactor.

The invention also includes an in-situ method for sampling and measuring carbon black fineness in a process stream comprising
 (a) sampling carbon black particles in-situ from a process stream,
 (b) adjusting the carbon black sample to conditions suitable for LII,
 (c) measuring the fineness of the particles using LII,
 (d) correlating the LII fineness measurement with actual particle fineness.

The invention further includes an in-situ method for sampling a particle-containing stream for LII-based particle fineness measurement comprising
 (a) sampling a particle-containing stream,
 (b) adjusting the sample to conditions suitable for LII, wherein the sampling is done with a sidestream.

The invention additionally includes a method for sampling a carbon black stream for LII-based measurement of particle surface area comprising
 (a) drawing a sample of carbon black from the stream,
 (b) adjusting the sample to conditions suitable for LII, and
 (c) providing the adjusted sample to an LII system for particle surface area measurement.

Still further the invention includes a method for controlling particle fineness during production of flame generated particulates comprising
 a) sampling the flame generated particulate in-situ in the production process,
 b) adjusting the flame generated particulate sample to conditions suitable for LII,
 c) measuring particle fineness of the adjusted particulate sample using LII,
 d) sending a signal related to LII-measured particle fineness to a controller,
 e) comparing the particle fineness signal to a set point, and
 f) sending a signal from the controller to adjust operation of the flame generated particulate production process.

The method of control may adjust the operation of the carbon black production process via control of the air/feedstock ratio.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE INVENTION

Figure 1:
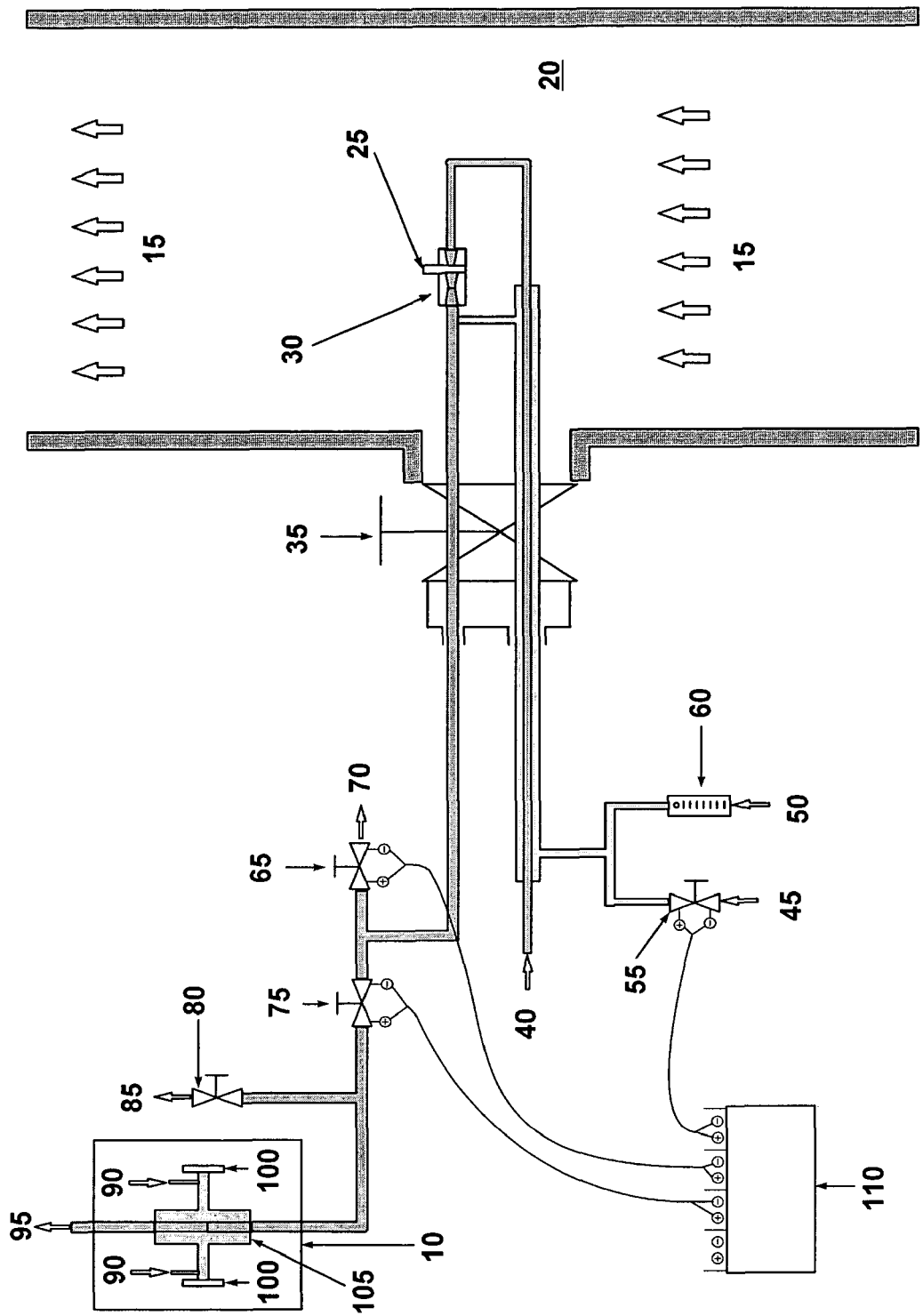
FIG. 1 shows a schematic of one specific embodiment of the carbon black sampling system.

Before the present compounds, compositions, articles, devices, and/or methods are disclosed and described, it is to be understood that this invention is not limited to the specific embodiments, specific embodiments as such may, of course, vary. It is also to be understood that the terminology used herein is for the purpose of describing particular embodiments only and is not intended to be limiting.

It must be noted that, as used in the specification and the appended claims, the singular forms "a," "an," and "the" include plural referents unless the context clearly dictates otherwise. Thus, for example, reference to "an eductor" includes more than one eductor, reference to "a stream" includes two or more such streams, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings:

"Fineness" as used herein means specific surface area of the particles.

"Size" as used herein means primary particle diameter.

"Suitable for LII" as used herein means those conditions that are proper or appropriate for a given LII instrument and/or system to provide accurate measurements for a sample to be measured by LII, such as the range of appropriate dilution or temperature conditions at which the particular LII system best operates.

"Reactor" as used herein can refer to all sections of the reactor (e.g., combustion, reaction, choke, and quenching sections) and also including the breeching section prior to the downstream equipment, such as a filter (bag) collector.

"Breeching section" as used herein means the ducting connecting the carbon black reactor to the next downstream equipment, like a filter collector.

The carbon black "smoke" is the stream of gas with suspended carbon black that exits the carbon black reactor and travels to downstream equipment, like a filter collector.

"On-line" as used herein means occurring in place (at a location substantially identical to the location at which the measurement is desired) without substantial disruption of the process.

"Real-time" as used herein means providing information regarding conditions at essentially the time at which those conditions are occurring, for example, with only a few seconds or tens of seconds of delay.

As used herein, the use of "measure" when referring to specific surface area of a particle can mean actually measuring particle size and correlating the particle size to the specific surface area.

"Optional" or "optionally" means that the subsequently described event or circumstance may or may not occur, and that the description includes instances where said event or circumstance occurs and instances where it does not.

By the term "effective amount" of a composition or property as provided herein is meant such amount as is capable of performing the function of the composition or property for which an effective amount is expressed. As will be pointed out below, the exact amount required will vary from process to process, depending on recognized variables such as the composition employed and the processing conditions observed. Thus, it is not possible to specify an exact "effective amount." However, an appropriate effective amount may be determined by one of ordinary skill in the art using only routine experimentation.

It is desired to provide, real-time, on-line sampling and LII fineness (particle surface area) measurements of carbon black while it is being manufactured.

The current method of determining carbon black fineness during the manufacturing process is to collect a sample, take it to the lab, and then determine the fineness via $I_2$ or $N_2$ absorption methods. This gives a delay time of at least about an hour.

The present invention provides methods for in-situ sampling of particles, in-situ sampling and measurement of particle size using LII, and methods of controlling carbon black processes using in-situ sampling and measurement of particle fineness using LII.

Though the current invention refers to the methods in terms of carbon black, the concepts can be adapted by one of skill in the art to any particle process. For example, other flame generated particulates, such as titania or silica, can be amenable to the method of the present invention as well.

Method of Sampling

The invention includes a method of sampling for measuring particle fineness. Specifically, the method can measure the fineness, or particle surface area, of carbon black. Specifically, the method can use laser-induced incandescence (LII) to measure the particle fineness.

The invention includes an in-situ method of sampling a particle-containing stream for LII-based particle fineness measurement comprising (a) sampling in-situ a particle-containing stream, and
(b) adjusting the sample to conditions suitable for LII.

The method may further comprise the steps of (c) measuring the adjusted sample using LII, and
(d) correlating the LII measurement with actual particle fineness.

The particles, such as carbon black, can be sampled from a process stream. The process stream can be within a carbon black reactor, or other location within a carbon black production process.

Sampling

Sampling particles is the first step of the method. Sampling can be accomplished in-situ without disturbing the process. Preferably, sampling is done automatically without human intervention. Sampling is performed at a desired location in the process and at desired time intervals. One of skill in the art can determine appropriate locations and intervals for a particular application. Theoretically, sampling can be done at any desired location in the process. For carbon black reactor control, the breeching section of the reactor is the most logical location.

A couple of trials were conducted at actively operating carbon black production facilities. Full commercial size reactors were used for the testing. Although some difficulties with sampling were encountered with early trials, the trials were successful in showing that the LII technique could be used to measure carbon black fineness. The last trial solved the sampling difficulties.

Carbon black was first attempted to be measured directly in the breaching section of the carbon black reactor using a window into the reactor for optical access and LII. Since this did not prove successful, a sidestream (slip stream) of carbon black was pulled from the reactor.

Measuring the sidestream for carbon black also proved not as successful as hoped due to plugging.

Therefore, a sidestream was pulled and this sidestream was diluted (FIG. 1). The LII measurements were then done at ambient conditions to the diluted sidestream. Dilution is discussed in the ADJUSTING section. LII measurement is discussed in the MEASUREMENT section.

Contents under pressure can be sampled, for example, by simply providing an opening in a container (e.g., reactor) which holds the particles and capturing or directing the stream which exits the opening into the sidestream. This can be supplemented by extraction methods if desired.

Contents not under pressure may need to be extracted from the container (e.g., reactor) into the sidestream such as by creating a pressure differential to collect the particles. One of skill in the art can determine equipment appropriate for extracting or creating a pressure differential. For example, carbon black can be sampled from a carbon black reactor by placing a port in the reactor or utilizing an existing opening in the reactor. A probe can be placed in the reactor at a location within the reactor that would capture particle samples representative of the carbon black process stream within the reactor. For example, the probe can be placed far enough into the reactor that wall effects, such as carbon black buildup, can be avoided. The remainder of the sampling equipment can be placed outside the reactor. Preferably, sampling and dilution are done with a configuration wherein the sampling device (in this case, eductor and orifice) is located inside the reactor or breeching section (where the temperature is high) at a location which yields representative samples as opposed to diluting the sample outside the reactor or breeching section.

Various methods and devices can be used for extraction into the sidestream. For example, an eductor can be used to extract sample through a probe within the reactor, if a probe is used. Preferably, for example, a venturi eductor with a critical (sonic) orifice on the sample inlet of the eductor can be used to induce a subatmospheric pressure at the sample inlet. One of skill in the art would be able to determine appropriate methods and devices for a particular application.

One of skill in the art would be able to determine equipment that adequately extracts a sample of desired size. One of skill in the art would be able to determine an appropriate location within the process to extract a sample.

In initial tests, a small probe was inserted into the "smoke" stream and a sample was sucked out into the sidestream and diluted using an air-driven eductor. An optical cell was used to make the LII measurements. Measurement is discussed below.

In the latest test, a venturi eductor with a critical orifice on the sample inlet of the eductor was inserted into the "smoke" stream and sample was sucked in and diluted using primary motive air to the eductor. The sample was diluted with secondary dilution air and then measured using LII. Dilution is discussed in ADJUSTING, and measurement is discussed in MEASURING.

Embodiment of Carbon Black Sampling System

There were three main design considerations for the carbon black sampling system: draw a representative carbon black sample, dilute the sample to approximately less than or equal to 1 ppm (optimal concentration for LII signal detection provides a signal with excellent signal to noise ratios and minimal LII signal attenuation as the LII signal propagates through the sample volume), and deliver a steady-state gas sample to the LII sample cell. Dilution is discussed in the ADJUSTING section below.

In a successful test case, a small stream of carbon black was continuously extracted from the reactor just prior to the heat exchanger (i.e., the breeching section of the reactor). The carbon black was extracted from a carbon black reactor using a venturi eductor (e.g., Fox valve; 0.060" orifice) connected to steel tubing. The steel tubing was inserted into the breeching section approximately 3–12 inches past the edge of the refractory wall into the stream of carbon black "smoke." Compressed air was used to operate the venturi eductor.

In a second test case (FIG. 1), a small stream of carbon black was continuously extracted from the reactor in the breeching section 20 of the reactor. The carbon black was extracted from a carbon black breeching section 20 using a venturi eductor 30 (e.g., Fox Valve, Dover, N.J.) with a critical (sonic) orifice 25 (e.g., Lenox Laser, Glen Arm, Md.). The eductor 30, orifice 25, and piping enter the breeching section 20 through a valve entry 35. The venturi eductor 30 was utilized to induce a subatmospheric pressure at the sample inlet. The critical (sonic) orifice 25 was utilized on the sample inlet of the eductor in order to control the flow rate of the carbon black. The critical orifice 25 size used in this particular test was about 300 microns. The size of the critical orifice 25 can be changed for a desired sample pull (e.g., carbon black concentration). Typically, small tubes/openings that transport carbon black smoke 15 tend to foul and plug. In order to keep plugging from occurring two approaches were used. The high gas velocities (sonic) in the critical orifice 25 greatly reduced the tendency to plug with carbon black. Also, the venturi eductor 30 and the sonic choke 25 were located in the breeching area 20 of the reactor where the temperature is high (e.g., about 1100° F.), as opposed to locating the eductor 30 and choke 25 outside the reactor at atmospheric conditions. This allows dilution to occur at high temperatures, reducing the thermophoretic forces that tend to make carbon black adhere to surfaces, and also eliminates moisture condensation that would occur due to expansion cooling as the gases pass through the orifices. Further, after dilution, the carbon black concentration was low and the gas dry, making fouling/plugging of the tubing in the system less of an issue. In addition to the a) size of the critical orifice 25 and b) the primary dilution air (primary motive air to the eductor) 40 flow rate, the use of secondary dilution air 50 (with a flow meter 60 on the line) was an additional control of the carbon black concentration. The use of secondary dilution air 50 flow allows the gas velocity in the tubing to be increased, thereby decreasing fouling of the sample tubing with carbon black.

The use of solenoid valves 55 (normally closed), 65, 75 controlled by a programmable timer 110 allowed the system to be cleaned/purged at regular intervals. The intervals used in this particular test was a cleaning/purge cycle of about 60 seconds, with the purge time being about 6 seconds and the "good" sampling time being about 54 seconds.

The use of two solenoid valves on the sample outlet (valves 65 (normally closed) and 75 (normally open)) allowed the high pressure pulse to be dissipated to the atmosphere, thereby protecting the LII sampling cell 105 within the instrument 10 from high pressures. Without the use of solenoid valve 65 to vent the pulses (vented pulse 70), the high pressure pulses tended to "overwhelm" the window 100 purge system (optical cell window purge 90), causing the optical windows 100 to become fouled.

The particular embodiment in FIG. 1 also allows bypass of the LII instrument 10 directly to the atmosphere (vent air 85) through a by-pass valve 80.

During the cleaning/purge cycle, the LII measurement is not representative of the process. Therefore, it is necessary to eliminate this data from the "rolling average." This can be done in a variety of ways. This is discussed below.

The main components of the early embodiment of the sampling system were a 76-inch long stainless steel probe (¼-inch outside diameter/0.175-inch inside diameter) and a pair of Fox 611210-060 eductors.

The tip of the stainless steel probe was inserted through a packing gland in the wall of the carbon black reactor at a location near the entrance of the heat exchanger, approximately 80 feet from the reactor fuel nozzles. This represented a residence time of approximately 0.75 sec from oil (carbonaceous feedstock) injection to the probe location. The tip of the probe was inserted approximately 6 inches into the reactor gas stream.

The initial tests of the sampling system indicated that the carbon black sample concentration significantly exceeded the desired 1 ppm range. An additional metering valve was inserted after the second eductor to generate an upstream backpressure that reduced the amount of carbon black sample drawn from the reactor.

A slip stream (sidestream) sample was drawn from the reactor by a two-stage dilution system using the Fox eductors (0.060-inch/1.5 mm diameter orifice) supplied with 60 to 80 psig shop air. The dilution performed several functions: it reduced the carbon black concentration to a 0.2–0.4 ppm range, reduced the sample gas temperature, and reduced the amount of water in the sample, which prevented condensation of water vapor on the sample cell windows. With the final concentration of 0.2–0.4 ppm, and a concentration of the reactor gas stream, once cooled to ambient, of 50–100 ppm, the dilution was approximately 250 parts dilution air to 1 part reactor gas.

The sampling system contained a set of valves that could redirect the air to purge the sample probe if it became plugged or divert the gas away from the LII sample cell. The total length of the sample system was approximately 49 feet. Most of the sample system gas line was ½-inch outside diameter plastic tubing. This relatively large diameter was selected to reduce the possibility of obstruction. The final 10-inch length of aluminum tubing of the sample cell had an outside diameter of 0.375-inches and an inside diameter of 0.344-inches.

For the most part, the sampling system delivered a steady state carbon black gas sample at the desired concentration. The concentration was kept below about 0.5 ppm to minimize attenuation of the laser and signal beams through the cell. This is not a requirement, but simplifies processing, as no correction for the attenuation needs to be performed in the analysis for these lower concentrations.

The preferred embodiment of the carbon black sampling system of the present invention is shown in FIG. 1 as described above.

Sampling Issues

Issues that arose during the early trials were primarily concerned with sample line obstruction. As expected, sampling of the carbon black from the reactor in a consistent manner was difficult. The valves and restrictions within the sampling lines tended to plug with carbon black. A metering valve used downstream of the second eductor was especially prone to plugging. The plugging of the metering valve was evident in LII data by observing a gradual decrease in the carbon black volume fraction (soot concentration).

It was observed that obstruction of sampling lines was more frequent on days when it rained, cooling the lines substantially, and, thus, increasing thermophoretic effects. Heating the sampling line can reduce the frequency of obstructions in these sorts of sampling systems.

Heating the first eductor (described below in ADJUSTING) may also reduce chances of plugging the sample line. Heating of the eductor may also reduce chances of condensation.

These problems did not occur in the preferred embodiment of FIG. 1.

Adjusting

As discussed above, direct LII measurement of carbon black in the reactor was not successful due to the concentrations of carbon black in the process streams and the other harsh conditions of the reactor. Adjustment of the samples provided not only the ability to better measure the particles using the LII measurement system, but helped alleviate sampling system problems such as plugging.

Engine emissions are relatively dilute (low concentration) streams of soot. No dilution is needed for measurement of these streams as seen in the art on LII measurement of engine emissions. However, this is rarely, if ever, the case with carbon black streams during production. Therefore, adjustment is needed for carbon black prior to measurement with LII.

Also, the precision requirements for particle fineness measurements for the carbon black industry are an order of magnitude greater than those for emissions research.

Adjustment of the sample can be done. Adjustment may be necessary to provide the samples in a condition suitable for LII. For example, concentration can be an issue with utilization of LII instrumentation and methods. Temperature can also be an issue.

Adjusting the sample can be done, for example, by diluting the sample. The sample can be diluted to a concentration of less than about 3 ppm or less than about 2 ppm. Specifically, the sample can be diluted to a concentration of about less than or equal to 1 ppm. The sample can be diluted, for example, to a concentration of about less than or equal to about 90, 80, 75, 70, 60, 50, 40, 30, 25, 20, 15, 10, 5, 3, 2, 1, 0.7, 0.5, 0.4, 0.3, 0.2, or 0.1 ppm. The sample can be diluted to about the concentration of the detection limit of the LII instrumentation and methods. One of skill in the art would be able to determine a concentration level that is appropriate for a given LII system. Adjusting the sample can occur simultaneously with sampling or subsequent to sampling, for example.

In the case of a particle stream, such as carbon black, which is in air, the dilution may be accomplished by addition of more air. Specifically, a stream of carbon black pulled from a carbon black reactor can be diluted using an eductor. Further, secondary dilution can be used in addition to primary dilution.

Dilution can simultaneously bring the sample conditions to ambient temperature.

In the trials performed, the stream was diluted with air. Dilution in the early test case was used for two reasons:
(1) to ensure moisture did not condense on the optical windows, and (2) the optimal volume fraction for the LII measurement technique was approximately 0.5 ppm, whereas the volume fraction of the cooled undiluted carbon black stream would be approximately 100 ppm.

In the early test case, it was found that for the particular eductors used, 2 eductors were needed to get adequate dilution for the particular carbon black reactor stream, LII instrumentation and methods used. The first venturi eductor that was used did not provide sufficient dilution (carbon black concentration was still too high). Therefore, an additional eductor was placed in series following the first eductor and prior to passing to the LII instrumentation (2-stage dilution).

Any number of eductors in series may be used in order to get the desired dilution. Alternatively, eductor(s) with a higher dilution ratio (e.g., one by Dekati) can be used.

Another option in the dilution process is to route the outlet of a dilutor back to the reactor such that the reactor pressure does not effect the dilution.

An attempt to reduce the particle concentration was made by restricting the venturi inlet from the carbon black reactor, but that method was unsuccessful. It was found that the restriction would plug very quickly with carbon black. Therefore, the second eductor was used to sample from the output of the first eductor.

The outlet of the second eductor was also restricted with a metering valve.

In the last test case, a primary dilution and a secondary dilution were used.

Based on the carbon black concentrations present in the early test case, the overall dilution was approximately 200–250:1, i.e., 250 parts compressed air to 1 part carbon black "smoke" (on a standard gas volume basis).

The overall dilution ratio utilized for the last trial was about 350:1, resulting in a carbon black concentration (expressed as soot volume fraction, svf) at the point of measurement of about 150 parts per billion (ppb). A volume fraction of up to 1 ppm (or 1000 ppb) was utilized, but lower svf decreases fouling and plugging problems. As the sensitivity of the LII instrument can be increased the svf can be decreased. Lowest concentration is dependent upon the signal/noise ratio of the LII instrument.

One of skill in the art would be able to determine the appropriate dilution ratio required for a particular application. Based on the dilution ratio, an appropriate eductor or eductors or additional dilution streams can be selected to provide the ratio.

One of skill in the art would be able to determine the appropriate temperature required for a particular application.

Based on the conditions and concentrations of the particle samples and the requirements for a particular LII system, one of skill in the art would be able to determine appropriate adjustment steps to accurately measure the particle sizes using LII.

Measuring

This optional step is discussed below.

Correlating

This optional step is discussed below.

Method of Measuring Particle Fineness

The invention includes a method for measuring particle fineness. Specifically, the method can measure the fineness, or particle specific surface area, of carbon black. The method can measure fineness of other particulates as well, such as titania or silica. Specifically, the method can use laser-induced incandescence (LII) to measure the particle fineness.

The invention includes an in-situ method for sampling a particle-containing stream and measuring particle fineness using laser-induced incandescence (LII) comprising a) sampling particles in-situ, b) adjusting the sample to conditions suitable for LII, c) measuring the adjusted sample using LII, and d) correlating the LII measurements with actual particle fineness.

The particles, e.g., carbon black, can be sampled from a process stream. The process stream can be within a carbon black reactor, for example.

In order to use a LII measurement process for carbon black in-situ and real-time within a carbon black process, the sample needs to be pulled and prepared in a way that is reliable, does not disturb the carbon black process, and is ready for measurement by LII. This is done via sampling and adjusting steps.

Sampling

Sampling particles is the first step of the methods. Sampling is discussed above.

Adjusting

Adjustment of the sample can be done. Adjustment is discussed above.

Measuring

Once the particles are sampled and adjusted, they can be measured for particle fineness using an LII system.

Measuring the adjusted sample using LII can be accomplished using various LII instrumentation and methods, such as those discussed in the BACKGROUND for measuring particle fineness. As discussed above in the BACKGROUND section, various LII instruments and methods are known. One of skill in the art would be able to determine instrumentation, software, and modifications needed to measure the adjusted sample using LII.

A system that has been used to measure particles of carbon black sampled from a carbon black reactor and adjusted for concentration is described below.

Once the carbon black stream was sampled from the reactor and adjusted (diluted and cooled), the adjusted sample was delivered to the LII instrumentation via ½ inch plastic tubing, in the early test case. Specifically, the adjusted sample was delivered to an optical cell within the LII instrument.

Figure 2:
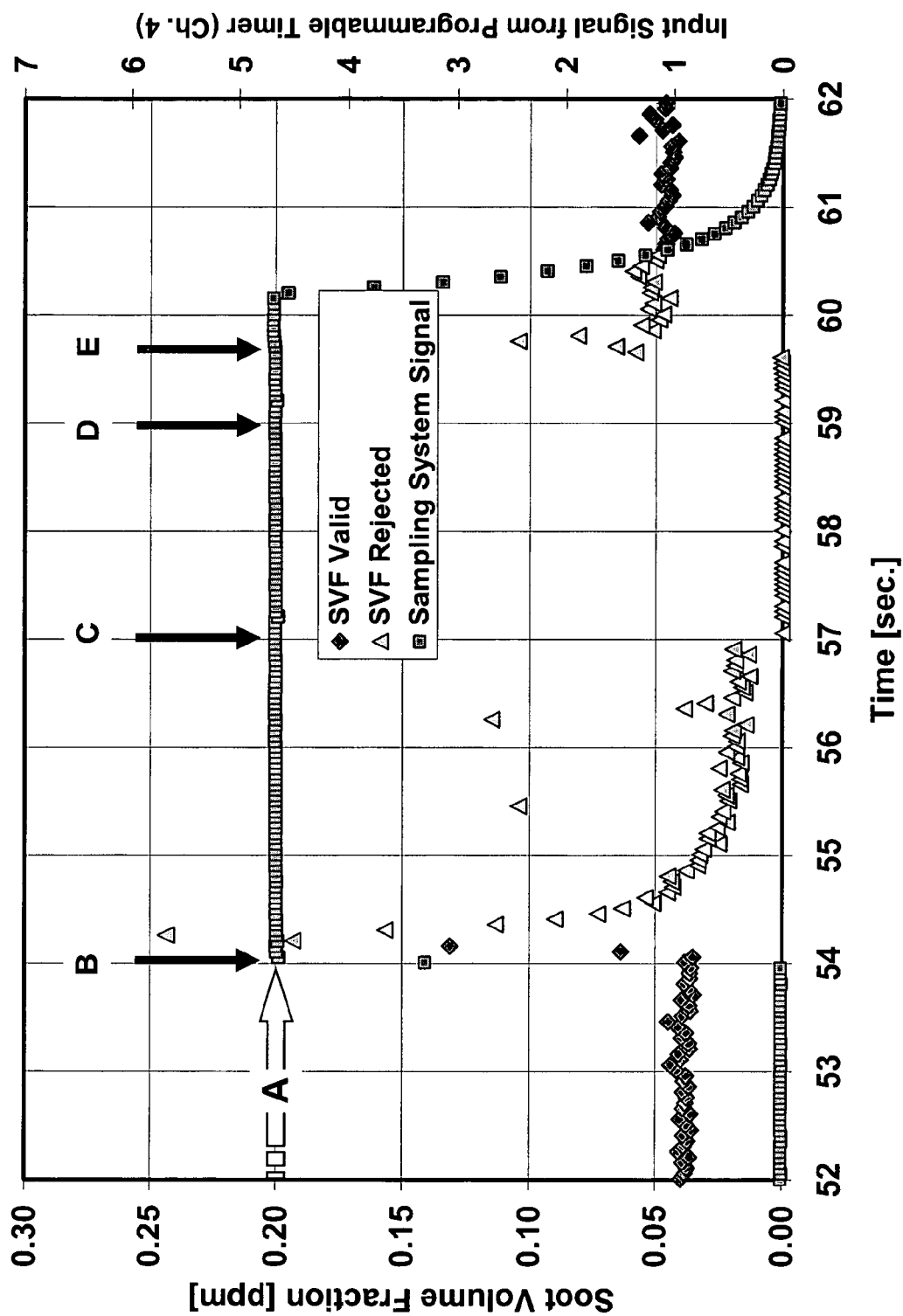
FIG. 2 is a graph from a trial of the measured soot volume fraction (svf) and the input signal from a programmable timer 110 on the system of FIG. 1. The timer signal is used to reject invalid data during a purge/cleaning cycle of the sampling system. Time period A is normal operation from t=0 to 54 sec. Valves 55 and 65 are closed and valve 75 is open. Time B at t=54 sec is when valve 55 opens. At time C (t=57 sec), valve 75 closes. At time D (t=59 sec), valve 65 opens and valve 55 closes. At time E (t=60 sec), valve 75 opens and valve 65 closes. After t=60 sec, the 5 period (A–E) cycle is repeated.

The preferred method of eliminating the data acquired during the cleaning cycle is to utilize a signal from the programmable valve timer to indicate when data should be ignored. This is shown in FIG. 2.

During the trial, the data acquired during the cleaning cycle was eliminated by "filtering" the data based on several criteria:

1) Soot volume fraction (svf) too low (below a user-selected threshold)

2) Peak signal (on either detector) too low (below a user-selected threshold)

3) Peak signal too high—analog-to-digital board saturated

4) R-squared test—ln (T-$T_{gas}$) vs time should be linear. If $R^2$<user-selected threshold, ignore data.

5) If either svf or LII surface area are outside of mean ±factor*standard deviation, ignore data (factor was user selected, but usually 2.0–2.5).

LII System

A standard LII system can comprise a number of components including a laser, transmitting optics, receiver optics, detectors, and calibration systems. Instrumentation is commercially available or can be constructed by one of skill in the art. One of skill in the art would be able to determine components necessary and suitable for a particular LII application.

An example of a LII apparatus used for determination of primary particle size can be found in U.S. Pat. No. 6,181,419. Other LII apparatuses may be assembled or constructed by one of skill in the art.

Various parameters can be set and adjusted within an LII system. One of skill in the art of LII can determine those parameters and operating conditions.

For example, the beam profile can be determined by one of skill in the art for a particular application. Sufficient amount of light energy for a desired application can be determined by one of skill in the art, such as laser energy per pulse and the wavelength.

Given the particle laden environment (carbon black production plant) in which the instrument must operate, the enclosure around the LII system is preferably light and dust tight.

In the test cases, a sample cell was designed and fabricated. The design incorporated features that would ensure the delivery of a stable gas sample, minimize the possibility of optical window contamination and minimize light scattering. The main feature of the sample cell was a sample delivery tube with an inside diameter optimized for the LII signal collection volume, a sample chamber that maintains a laminar gas flow through the cell, main sample chamber orifices for the laser beam and LII signal sized to minimize the solid angle over which scattered light can be detected, surfaces to reduce light scattering, laser beam input and output windows mounted to minimize laser beam transmission losses and reflections, gas purge ports located near the inside window surfaces to prevent contamination that would reduce the LII signal, quick release window mounts to reduce the time required to remove windows for inspection or cleaning, and, finally, a segmented design that allows sections to be removed to access the sample volume location (for optimum cell alignment relative to excitation laser beam and LII signal collection axis) and ensures that all surfaces of the sample cell can be cleaned, if required. One of skill in the art of LII would be able to determine an appropriate sample cell for use in a system. Once the conditions of use are determined an appropriate cell can be purchased or fabricated.

The optics will ideally be designed so that no operator intervention is required during the normal operation of the system.

The system preferably has a digital oscilloscope and converter of the appropriate characteristics, which can be determined by one of skill in the art.

The LII system is relatively robust and does not require extremely precise optical alignment, laser power controls, and detector gain settings. However, adjustments may be made as necessary as the sample changes or the carbon black concentration changes in the sampling line.

Data acquisition and management software for the LII system can be, and is preferably, used. The software can be built around the client-server paradigm for remote and local access to instrument set up, data acquisition and analysis. The software can perform correlation calculations to output a signal or display of the desired variable, e.g., particle size.

One program can control the instrument. Another can contain the user interface and connect to a server or a controller.

One of skill in the art of LII can choose or fabricate an appropriate LII system.

Particle Size

In order to calculate the temperature of the particles, the incandescence signal can be measured at two different wavelengths, for example, wavelengths of 400 nm (blue) and 780 nm (slightly infrared). The incandescence signals from many laser pulses (typically 40 for the test experiments) can be averaged to reduce noise. (Alternatively, the calculated fineness results from each pulse can be averaged together rather than averaging the signals.) The incandescence signal (and therefore, the temperature) rises rapidly when the laser is pulsed. After the laser pulse ends (after approximately 20 ns), the particles begin to cool due to conduction/convection to the surrounding gas. The temperature is calculated from the ratio of the two incandescence signals. The slope of this temperature decay can be used to compute the carbon black fineness.

In the early test case, the incandescence signals became noisy after particle temperature dropped to <2500 K. For this reason, the average slope of the temperature decay between 200–600 ns was used to compute the particle size.

This sizing is based on first principles in modeling, relating the rate of decay of the temperature differential between the heated particles and the surrounding medium to the size of the primary particles. The model used assumed the heat transfer is from individual primary particles, not aggregates, and that these primary particles were monodisperse. However, carbon black particles are aggregated, and there is a distribution of both the primary particles sizes and the number of primary particles per aggregate.

A carbon black sidestream was pulled from the reactor to perform LII measurement on. The sidestream was diluted and cooled. The LII measurements were then done at ambient conditions to the diluted sidestream.

In addition to incandescence signals, scattering data can be collected to give information about aggregate size (since carbon black is generally found in aggregates of primary particles and not just individual primary particles). A combination of scattering and incandescence measurements can yield information about both fineness (size, surface area) and structure (aggregate size) of the carbon black.

Carbon black structure (aggregation) information can be gathered in an analogous manner to fineness information. Instead of incandescence measurements, the instrument would be modified to gather measurements on the scattered light of the laser pulse when hitting the particulate sample. This information would then be correlated to lab information much like the incandescence data.

Correlating

Particle size measured by LII is provided in terms of decay rates of either particle temperature or incandescence signals. To provide the measurements in terms of particulate fineness, this signal must be correlated to measured specific surface areas.

Correlating the LII measurement with actual particle size can be done automatically, e.g., with a computer, or by manual calculation using a function that correlates the two.

Previously, LII measurements of fineness have not been correlated with standard carbon black measurements. With the LII data gathered in the test cases, a correlation of this data with standard carbon black measurements was performed.

For each carbon black reactor trial, a carbon black sample was collected at a standard sample collection location downstream of the heat exchanger. Additional carbon black samples were acquired from the slip stream drawn from the reactor for the LII experiments. These samples were obtained from a filter sock trapping the sample probe by-pass location. The standard series of laboratory particle surface area tests were performed on these filter sock samples and compared to samples acquired at the normal sample location downstream of the heat exchanger; the analysis indicated that the two sample locations gave carbon black samples with virtually identical properties. Once it was known that each sample location would give virtually identical samples, the results of the two sample locations could be correlated.

Samples pulled directly from the reactor to the sidestream and measured by LII were correlated with samples pulled at the same time that were tested in the laboratory using standard methods for carbon black surface area measurement. The objective was to obtain an empirical correlation between the LII determined apparent primary particle fineness and the laboratory-determined specific surface area measurements.

The mean normalized specific surface area (NSSA) determined by LII was plotted versus measurements of oil rate, $I_2$ number, nitrogen surface area (NSA), and/or statistical thickness surface area (STSA) (ASTM D6556) to determine if there was a statistically significant correlation.

All the plots provided a reasonable to good correlation. The lowest for any trial was 0.90. In the later tests, correlations of about 0.98–0.99 were achieved.

As stated earlier, with the LII model used, the particles were treated as individual monosized primary particles, not accounting for the effects of a primary particle size distribution, and completely ignoring the effects of aggregation.

The difference between the correlation coefficients for the different surface area measurements ($I_2$ number, NSA, and STSA) is due to the different physical properties that the methods are measuring, and are influenced by effects such as porosity. It is well known in the carbon black industry that different surface area techniques give different results, these are especially affected by porosity and surface chemistry of the carbon black.

It is expected that $I_2$ number will be used for the correlation for controlling processes but one of skill in the art can choose an appropriate fineness measurement which gives an appropriate correlation.

For correlating light scattering data to a known lab measurement, it is expected the known measurement would be dibutylphthalate absorption (DBP) (ASTM D2414) or oil absorption number (OAN) (ASTM D2414).

Method of Controlling Carbon Black Process

As previously stated, there has been a long felt need in the industry for a method which can give on-line, real-time measurement and control of carbon black fineness. The present invention provides such a method.

The fineness level of carbon black can be controlled primarily through adjustment of the air/feedstock oil ratio to the carbon black reactor. As indicated above, carbon black fineness is currently measured by collecting a carbon black sample, taking it to a lab, and measuring the fineness level using an iodine or nitrogen adsorption test. The results of the test are then utilized to make a manual adjustment of the air/feedstock ratio. Therefore, the carbon black process is currently controlled using a crude feedback control loop, where the feedback is given by the lab measurement(s) and the control is effected by the plant operator. This crude feedback control loop has a delay time of at least about an hour (the time necessary to collect the sample and make the lab measurement).

Any variable of production can be controlled by a process controller. For the current conventional methods of producing carbon black and the input signal variable of product size, this controlled variable is the air/feedstock ratio which is controlled by adjusting valves which let in air and/or feedstock to the reactor.

The carbon black sampling and LII fineness measurement techniques described above can be used to provide real-time (with only a few seconds or tens of seconds delay) information. Therefore, the feedback of the LII measurement can be used to provide automated feedback control of the carbon black fineness level.

The invention includes a method of controlling a process based on particle size measurement. Specifically, the method can control a carbon black process. The method can control the process based on measurement of fineness, or particle surface area. The fineness, or particle surface area, can be that of carbon black. Specifically, the method can use laser-induced incandescence (LI) to measure the particle fineness.

The invention includes a method for controlling particle fineness during production of carbon black comprising
 (a) sampling the carbon black in-situ in the production process,
 (b) adjusting the carbon black sample to conditions suitable for LII,
 (c) measuring particle fineness of the adjusted carbon black sample using LII,
 (d) sending a signal related to LII-measured particle fineness to a controller,
 (e) comparing the particle fineness signal to a set point, and
 (f) sending a signal from the controller to adjust operation of the carbon black production process.

The method can additionally include the step of correlating the LII measurements to actual particle surface area.

The carbon black can be sampled from a process stream. The process stream can be within a carbon black reactor.

The method can be used for controlling particle fineness of other flame generated particulates as well, such as titania or silica.

Figure 8:
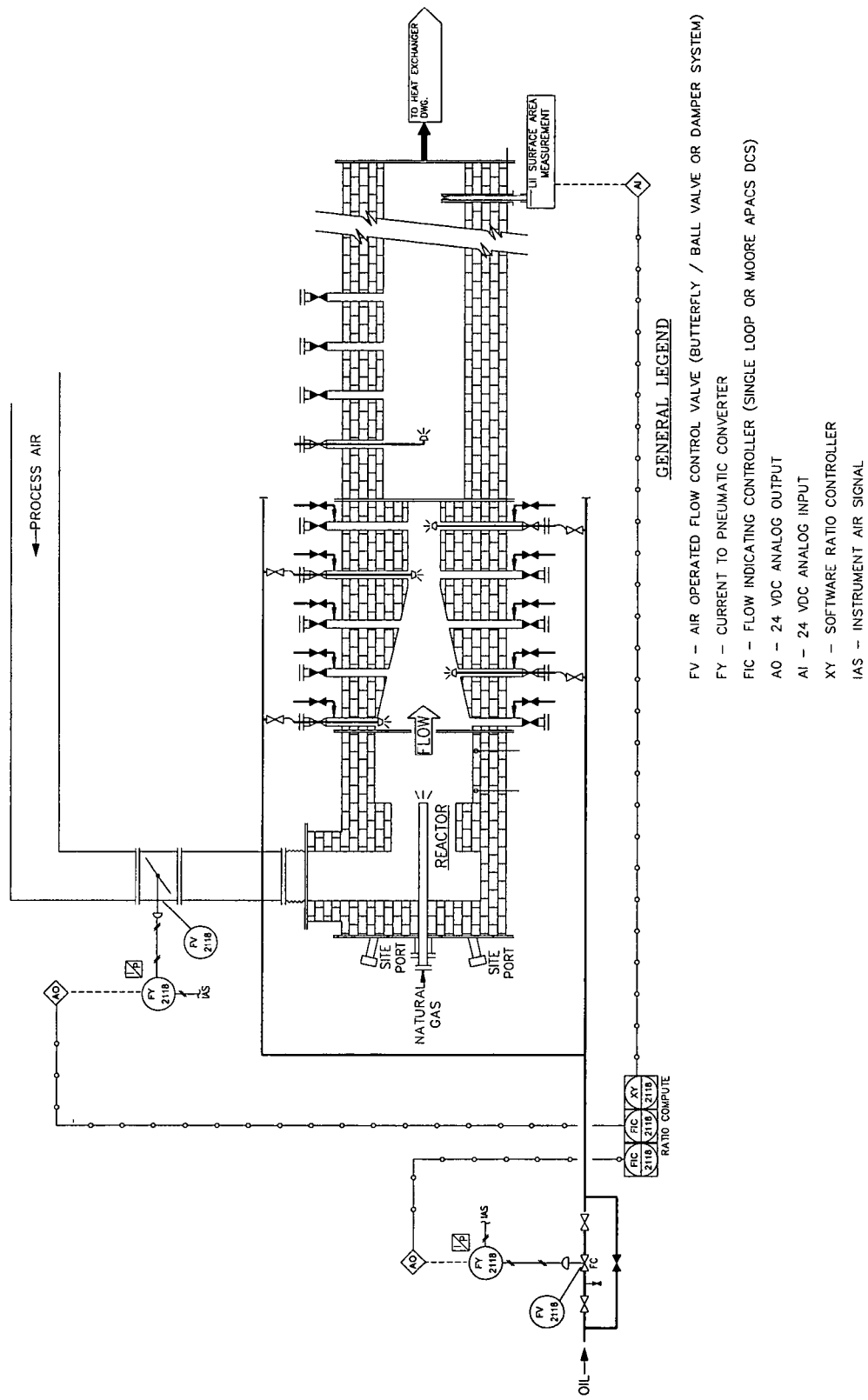
FIG. 8 shows one specific embodiment of a control diagram for controlling a carbon black reactor based on particle fineness measurements determined by LII.

An example of a specific embodiment of a carbon black reactor control schematic is shown in FIG. 8.

In the example control scheme, the LII measurement is compared to a target (set point) fineness level. If the measured fineness level is higher than the set point, the air/feedstock ratio would be decreased. If the measured fineness level is lower than the set point, the air/feedstock ratio would be increased.

The air/feedstock ratio is typically controlled by either keeping the air flow rate constant and varying the oil flow rate (through adjusting the oil control valve), or by keeping the oil flow constant and varying the air flow rate. However, both flow rates can be varied.

The potential benefits of using LII feedback control include, for example,
 tighter control of the carbon black fineness level, leading to a more uniform product,
 reduced production of off-specification material,
 quicker detection of upsets which could lead to better product uniformity, less product contamination, longer equipment life, etc.,
 reduced testing required in the lab, and quicker grade changes, leading to less off-spec/transition material.

One of skill in the art of process control can determine an appropriate control scheme for a particular process. Process loops other than feedback may be appropriate in certain processes and with certain equipment. Appropriate set point(s) and allowable variation for the process can also be determined for the desired carbon black product. Appropriate controllers (e.g., proportional, proportional-integral, proportional-integral-derivative) can be chosen by one of skill in the art.

Figure 3:
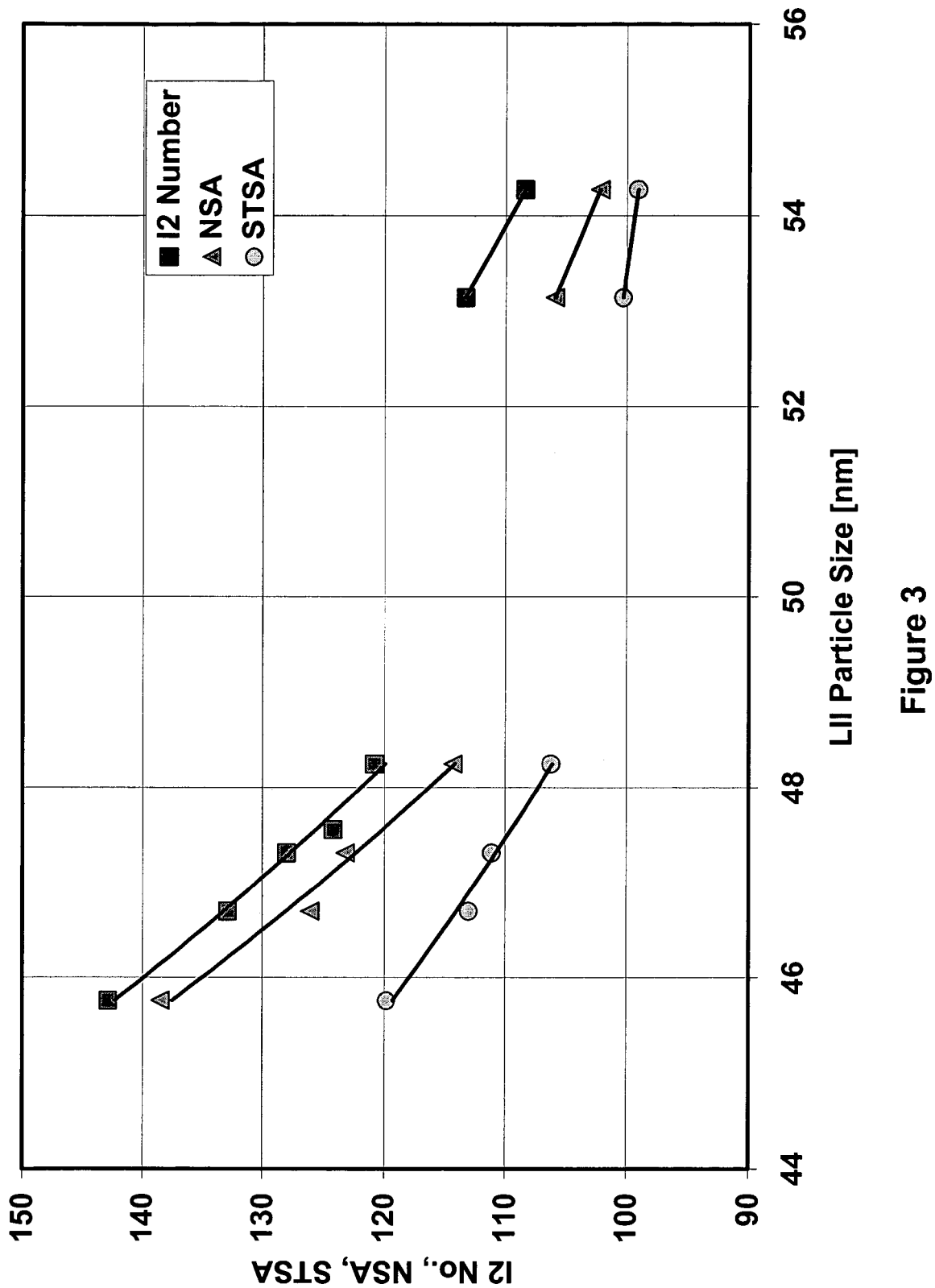
FIG. 3 is a graph mapping LII primary particle size to carbon black colloidal measurements (Iodine number ($I_2$ No., ASTM D1510), NSA (nitrogen surface area, ASTM D6556) and STSA (statistical thickness surface area, ASTM D6556)) during the trial. This particular sampling from this trial gives correlation coefficients of 0.9873, 0.9816, and 0.9848, respectively.

In a particular embodiment, the output of the LII instrument is utilized for feedback control of the specific surface area of the carbon black. The specific surface area is controlled by the overall ratio of hydrocarbon/oxidizer. Specifically, in the latest trial, the feedstock oil flow rate was controlled. The LII instrument utilized the signals from 2-color pyrometry analysis to determine a particle temperature in the few hundred nano-seconds after the laser pulse. The decay rate of the temperature was utilized to calculate the size (diameter) of the primary particles. The primary particle diameter was mapped to a colloidal surface area (using standard laboratory carbon black measurements). See FIG. 3.

Due to "noise" in the signal, it is desirable to average many data points to get a true representation of the carbon black surface area. In this control trial, a "rolling average" was utilized to represent the real-time specific surface area of the carbon black. The laser was pulsed at about 20 Hz, and a 3600 point rolling average was utilized. This means that the specific surface area indicated by the LII instrument represented an average of the previous 3 minutes. If the distribution of data can be tightened, a lower frequency of laser pulse can be utilized.

As described above, the data points acquired during the purge/cleaning cycle of the solenoid valves are not representative of the process. Therefore, it is desirable to reject these points and not have them influence the rolling average. The preferred method is to utilize a signal from the programmable timer utilized to control the three solenoid valves. (If plugging were monitored, this signal could be used to control the valves for the purge/cleaning cycle rather than simply putting them on a timer.) This was not possible during the trial, but would be possible with modifications to the LII instrument that was being used. In lieu of this method of rejecting data points, a series of criteria were utilized to filter/reject bad data points, as described above.

Figure 4:
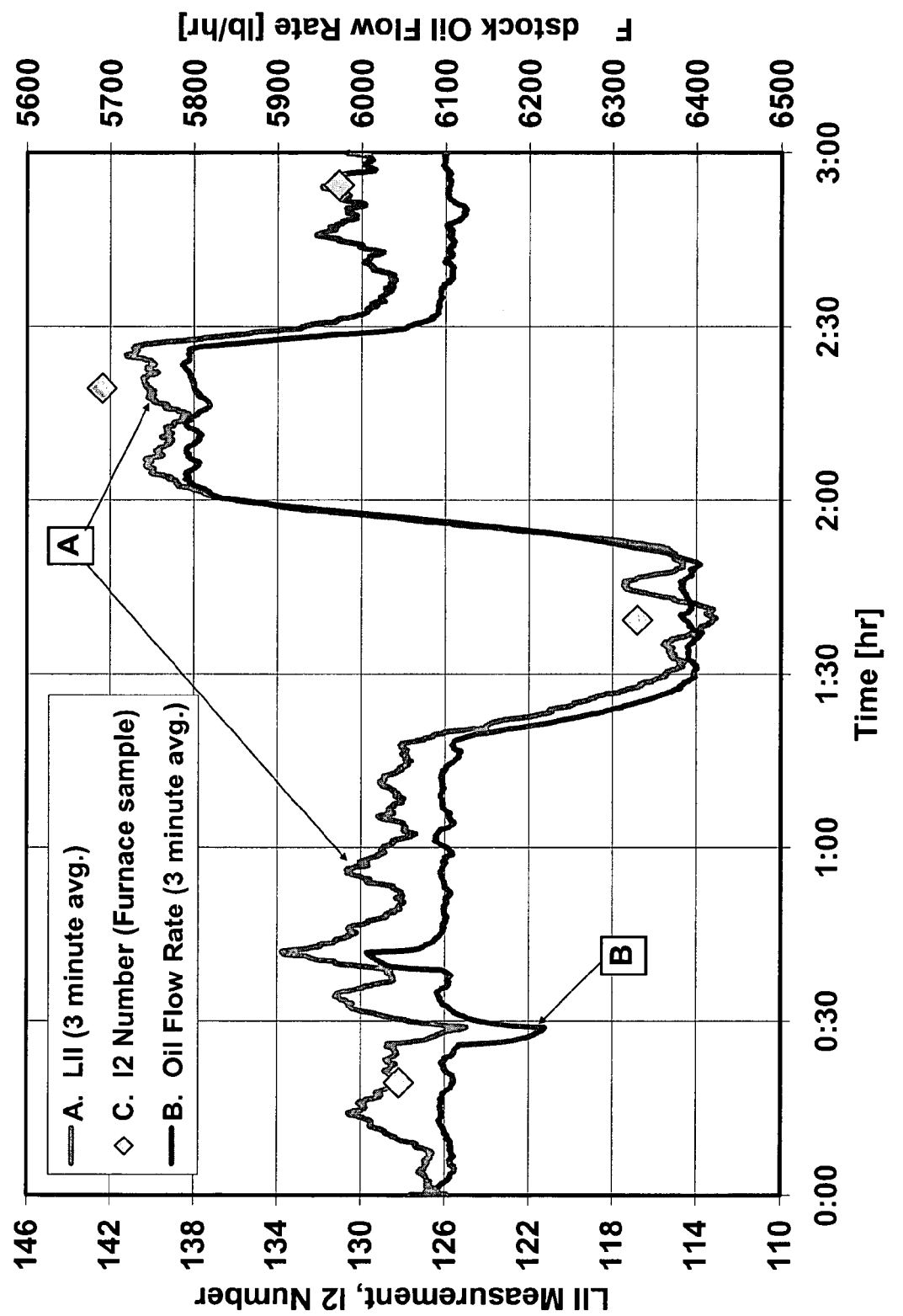
FIG. 4 is a graph showing an example of dynamic response of LII measurement to changes in oil flow rate to the reactor. Note: the oil flow rate scale is reversed.
Figure 5:
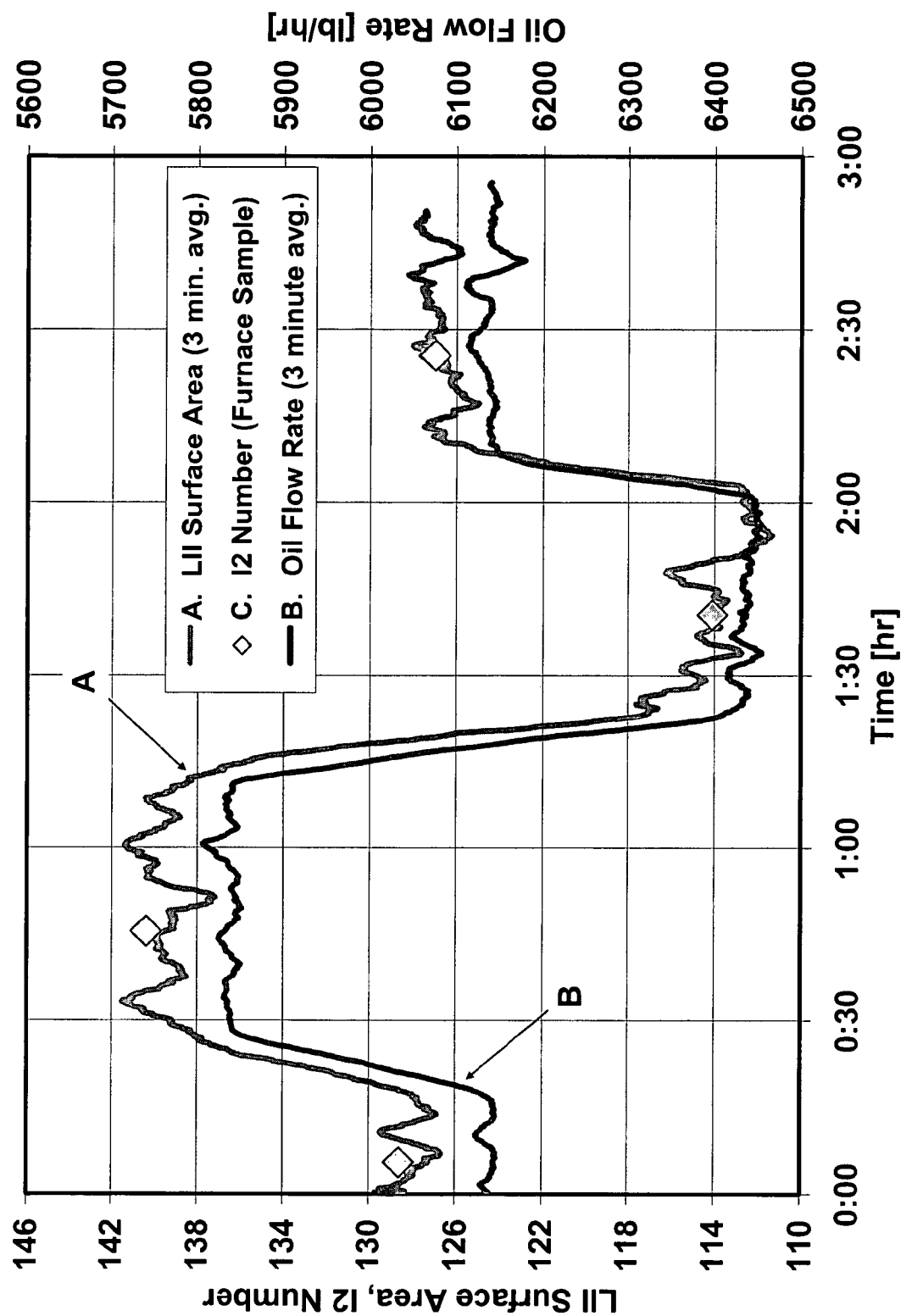
FIG. 5 is a graph of a second example of dynamic response of LII measurement to changes in oil flow rate to the reactor. Note: the oil flow rate scale is reversed.

Before utilizing the LII measurement for feedback control, it was necessary to verify that the LII signal would provide the appropriate temporal response to changes in the carbon black manufacturing process. This was done by varying the feedstock oil flow rate (while leaving the air, natural gas, and oxygen rates constant), since this would produce a change in the specific surface area of the carbon black. The temporal response of the LII measurement is shown in FIGS. 4–5. In FIGS. 4–5, the oil flow rate scale is reversed, since it is well known that an increase in oil rate (with all other parameters held constant) will lead to a decrease in the specific surface area of the carbon black. In FIGS. 4–5, the iodine number (a traditional carbon black measurement of specific surface area) was also compared to the LII measurement. The iodine number data points are represented by the diamond shapes on the graphs.

In order to test the feedback control, the reactor conditions were purposely perturbed by ramping the air and $O_2$ flow rates up and down. Since no similar changes were made in the oil flow rate, the carbon black specific surface area changed. The oil flow rate was then set on automatic feedback control, utilizing the LII measurement as the feedback signal. The feedback control of the process utilizing the LII signal is demonstrated in FIGS. 6–7. Controlling the oil flow rate in a feedback control loop (using the LII measurement as the input), the oil flow rate was automatically adjusted, thereby keeping the specific surface area relatively constant. Lab data was generated at various points to confirm the control.

Figure 6:
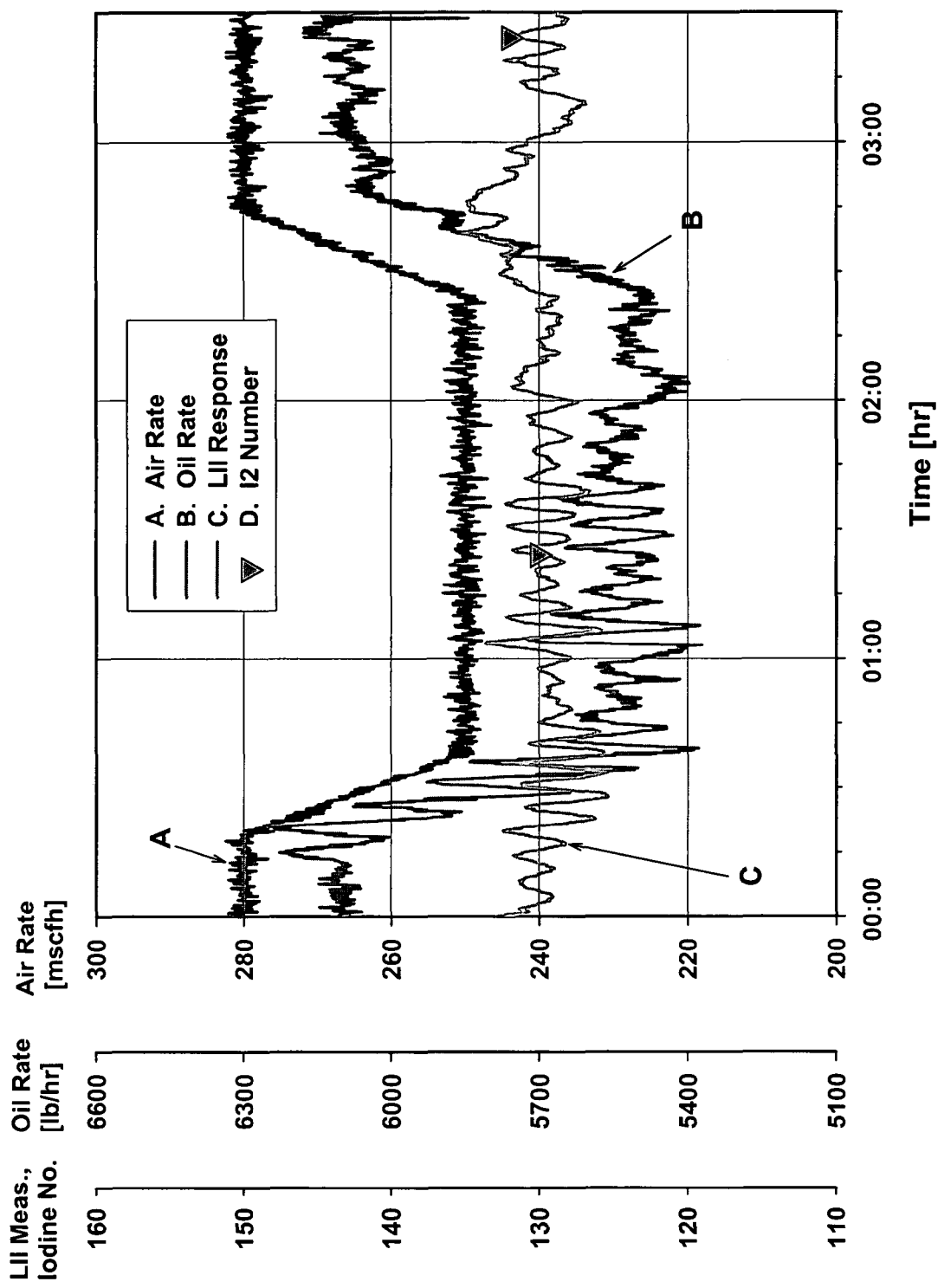
FIG. 6 is a graph of an example of feedback control of oil flow rate while air (and $O_2$) rate is ramped up and down. LII set point was 130.
Figure 7:
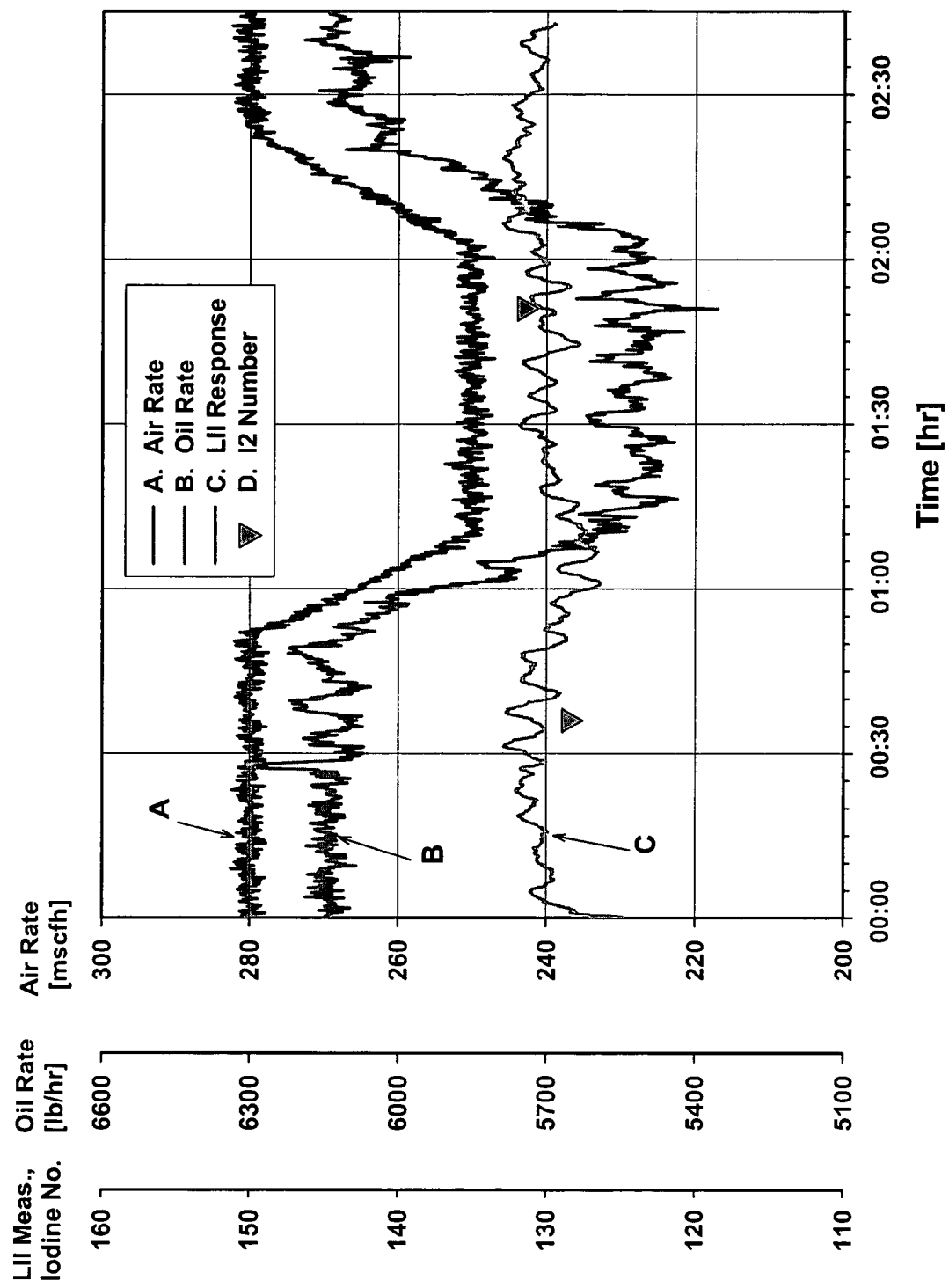
FIG. 7 is a graph of a second example of feedback control of oil flow rate while air (and $O_2$) rate is ramped up and down. LII set point was 130.

As seen in FIGS. 6–7, the "tuning" of the feedback loop was not optimized, since the oil flow rate and the LII signal exhibited some oscillation. Two factors which can improve fluctuations in the control are tuning of the controller and steadier power of the laser. Better controller tuning and steady laser power would reduce fluctuation in the LII signal.

Analogously to the control of particle fineness, particle structure (degree of aggregation), e.g., of carbon black, can be controlled. Structure information can be gathered as described above. The flow rate that would be controlled would be the additive that is used for control of structure, e.g., a potassium-based additive, in the case of carbon black. It is expected this would work for carbon black as well as other flame generated particulates where structure can be controlled such as by a flow rate of a reactant or additive.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An in-situ method for sampling a particle-containing stream and measuring particle fineness using laser-induced incandescence (LII) comprising
    a) sampling particles in-situ by drawing a sidestream from a source of the particles using an in-situ eductor with a sample inlet and an in-situ critical orifice on the sample inlet wherein the sample enters a sampling system through the critical orifice,
    b) adjusting the sample to conditions suitable for LII,
    c) measuring the adjusted sample using LII, and
    d) correlating the LII measurements with actual particle fineness.

2. The method of claim 1 wherein the adjusting comprises adding secondary dilution air to the sample.

3. The method of claim 1 wherein adjusting the sample to conditions suitable for LII comprises diluting the sample.

4. The method of claim 3 wherein diluting the sample is to a level of about less than or equal to 90, 80, 75, 70, 60, 50, 40, 30, 25, 20, 15, 10, 5, 3, 2, 1, 0.7, 0.5, 0.4, 0.3, 0.2, or 0.1 ppm.

5. The method of claim 3 wherein diluting the sample is to a level of about less than or equal to 1 ppm.

6. The method of claim 1 wherein adjusting the sample to conditions suitable for LII comprises bringing the temperature of the sample to ambient conditions.

7. The method of claim 1 further comprising determining a correlation function by comparing LII measurements and laboratory fineness measurements for particle samples drawn at the same time.

8. The method of claim 7 wherein the LII measurement is the decay rate of the LII intensity signal.

9. The method of claim 7 wherein the LII measurement is the decay rate of the temperature of the particles.

10. The method of claim 7 wherein the LII measurement is normalized specific surface area.

11. The method of claim 1 wherein the sampling and measurement of particle fineness is done in real-time.

12. The method of claim 1 wherein the sampling and measurement of particle fineness is done on-line.

13. The method of claim 1 wherein the particles are carbon black.

14. The method of claim 1 wherein the particle-containing stream is in a carbon black reactor or reactor breeching section.

15. The method of claim 1, wherein the in-situ sampling of a) is performed at a temperature above ambient conditions.

16. An in-situ method for sampling and measuring carbon black fineness in a process stream comprising
   a) sampling carbon black particles in-situ from a process stream by drawing a sidestream from the process stream using an in-situ eductor with a sample inlet and an in-situ critical orifice on the sample inlet wherein the sample enters a sampling system through the critical orifice,
   b) adjusting the sample to conditions suitable for LII,
   c) measuring the carbon black fineness using LII, and
   d) correlating the LII fineness measurement with actual carbon black particle size.

17. The method of claim 16 wherein the process stream is in a carbon black reactor.

18. An in-situ method for sampling a particle-containing stream for LII-based particle fineness measurement comprising
   a) sampling in-situ a particle-containing stream by drawing a sidestream from the particle-containing stream using an in-situ eductor with a sample inlet and an in-situ critical orifice on the sample inlet wherein the sample enters a sampling system through the critical orifice, and
   b) adjusting the sample to conditions suitable for LII, wherein the sampling is done with a sidestream.

19. The method of claim 18 wherein the stream is in a carbon black reactor.

20. The method of claim 18 wherein adjusting the sample to conditions suitable for LII comprises diluting the sample.

21. A method for sampling a carbon black stream for LII-based measurement of particle surface area comprising
   a) drawing a sample of carbon black from the stream by drawing a sidestream using an in-situ eductor with a sample inlet and an in-situ critical orifice on the sample inlet wherein the sample enters a sampling system through the critical orifice,
   b) adjusting the sample to conditions suitable for LII, and
   c) providing the adjusted sample to an LII system for particle surface area measurement.

22. A method for controlling particle fineness during production of flame generated particulates comprising
   a) sampling the flame generated particulate in-situ in the production process,
   b) adjusting the flame generated particulate sample to conditions suitable for LII,
   c) measuring particle fineness of the adjusted particulate sample using LII,
   d) sending a signal related to Lu-measured particle fineness to a controller,
   e) comparing the particle fineness signal to a set point, and
   f) sending a signal from the controller to adjust operation of the flame generated particulate production process.

23. The method of claim 22 further comprising correlating the LII-measured particle fineness to actual particle fineness.

24. The method of claim 22 wherein the flame generated particulate is carbon black.

25. The method of claim 24 wherein the adjustment of operation of the carbon black production process is via control of the air/feedstock ratio.

26. The method of claim 22 wherein the flame generated particulate is titania or silica.

27. An in-situ method for sampling a particle-containing stream and measuring particle fineness and aggregate size using laser-induced incandescence (LII) comprising
   a) sampling particles in-situ,
   b) adjusting the sample to conditions suitable for LII,
   c) measuring incandescence signals and scattering data for the adjusted sample using LII, and
   d) correlating the LII incandescence signals and scattering data measurements with actual particle fineness and aggregate size.

* * * * *

UNITED STATES PATENT AND TRADEMARK OFFICE
CERTIFICATE OF CORRECTION

PATENT NO. : 7,167,240 B2 Page 1 of 1
APPLICATION NO. : 10/622318
DATED : January 23, 2007
INVENTOR(S) : Stagg It is certified that error appears in the above-identified patent and that said Letters Patent is hereby corrected as shown below:

Column 20
Line 21, delete "Lu-measured" and substitute -- LII – measured --

Signed and Sealed this

Twenty-fourth Day of April, 2007

JON W. DUDAS
*Director of the United States Patent and Trademark Office*